United States Patent

Ballschuh et al.

[11] Patent Number: 5,101,046
[45] Date of Patent: Mar. 31, 1992

[54] 3-CHLOROMETHYLSULFONYLMETHYL-4-SULFOMETHYL-PYRROLIDINIUM-BETAINES AND PROCESS FOR THEIR PREPARATION

[76] Inventors: Detlef Ballschuh; Roland Ohme; Horst Seibt; Egon Gründemann, all of Institut für chemische Technologie, Patentbüro, Rudower Chaussee 5, O-1199 Berlin, Fed. Rep. of Germany

[21] Appl. No.: 629,135

[22] Filed: Dec. 18, 1990

[30] Foreign Application Priority Data

Dec. 21, 1989 [DD] German Democratic Rep. ... 336092

[51] Int. Cl.$^5$ .............................. C07D 207/08
[52] U.S. Cl. ..................... 548/570; 548/568
[58] Field of Search .................. 548/570, 568

[56] References Cited

U.S. PATENT DOCUMENTS

| 4,410,709 | 10/1983 | Ohme et al. | 548/409 X |
| 4,528,383 | 7/1985 | Schmitt | 558/73 X |
| 4,877,885 | 10/1989 | Ballschuh et al. | 548/409 X |

Primary Examiner—Joseph P. Brust

[57] ABSTRACT

The invention relates to novel 3-chloromethylsulfonyl-methyl-4-sulfomethyl-pyrrolidinium betaines (chloromethylsulfonyl-sulfobetaines) of the general formula I and to processes for the preparation thereof. The compounds according to the formula I can be used as organic intermediates for further syntheses or, if they contain a long-chain alkyl radical, as polyfunctional surfactants. Molar quantities of diallylammonium chloride are reacted with dichloroacetic acid and twice the molar quantity of sodium hydrogen sulfite in the presence of a catalytic quantity of a peroxodisulfate and, after the addition of a catalytic quantity of iodide, the reaction solution obtained is converted by heating to 3-chloro-methylsulfonylmethyl-4-sulfomethyl-pyrrolidinium betaines (chloromethylsulfonyl-sulfobetaines) of the general formula I.

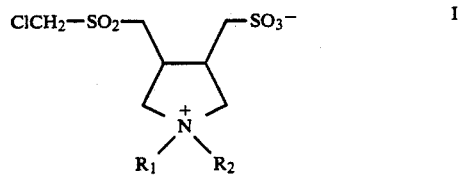

14 Claims, No Drawings

3-CHLOROMETHYLSULFONYLMETHYL-4-SULFOMETHYL-PYRROLIDINIUM-BETAINES AND PROCESS FOR THEIR PREPARATION

The invention relates to novel 3-chloromethylsulfonylmethyl -4-sulfomethyl-pyrrolidinium betaines (chloromethylsulfonyl -sulfobetaines) of the general formula I

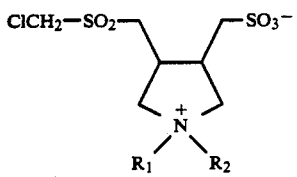

in which $R_1$ and $R_2$ are hydrogen, a straight-chain or branched alkyl radical having 1 to 22 carbon atoms or an alkyl radical which can contain the group —$CH_2$—$CONH$— at the start of the chain.

The novel chloromethylsulfonyl-sulfobetaines of the formula I represent, as organic intermediates of sulfobetaine character, a reactive component for further syntheses. If at least one of the substituents $R_1$ or $R_2$ is a long-chain alkyl radical, these compounds can be used as polyfunctional surfactants.

Chloromethylsulfonyl-sulfobetaines of the formula I and processes for the preparation thereof have not hitherto been disclosed. According to M. Kulka, J. Amer. chem. Soc. 72, 1215 (1950), however, chloromethyl aryl sulfones are known which are formed in the reaction of sulfinic acids with dichloroacetic acid, with addition of soda and decarboxylation. In this way, the corresponding chloromethyl aryl sulfone, for example, is obtained in 66% yield from p-chlorobenzenesulfinic acid after heating the aqueous solution of the components for 48 hours.

Very recently, novel sulfobetaine-sulfinic acids and salts thereof have become available as potential starting materials for the synthesis of chloromethylsulfonyl-sulfobetaines of the formula I.

Such sulfobetaine-sulfinates are obtained by free radical-initiated sulfocyclosulfination of diallylammonium salts with hydrogen sulfite according to DD 225,128 A1 and EP 163,319 A3.

Attempts, which were carried out according to the state of the art, for example, with sodium 1,1-dimethyl -3-sulfinatomethyl-4-sulfomethyl-pyrrolidinium betaine and sodium dichloroacetate (cf. Example 1), gave only unsatisfactory yields of the target product after a long reaction time, in addition to not completely convertible starting material.

The subject of the invention is a simple synthesis process for the preparation of 3-chloromethylsulfonylmethyl -4-sulfomethyl-pyrrolidinium betaines from sulfobetaine -sulfinates or precursors thereof, which allows the process steps to be carried out without isolation of intermediates and without formation of by-products, coupled with high purity and yield of the target product.

According to the invention, diallylammonium salts, preferably diallylammonium chlorides of the general formula II

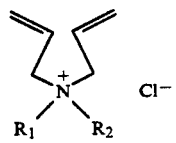

in which $R_1$ and $R_2$ are as defined above, are reacted in a first process step with molar quantities of dichloroacetic acid and twice the molar quantity of a metal hydrogen sulfite, preferably sodium hydrogen sulfite, in the presence of a catalytic quantity of a peroxodisulfate and, in the subsequent second process step, the reaction solution obtained is, after addition of a catalytic quantity of an iodide soluble in the reaction medium, heated at the boil until the sulfinate content of the reacting solution has fallen to virtually zero and the decarboxylation is complete.

The overall reaction, i.e. the free radical-initiated sulfocyclosulfination of the diallylammonium salt with coupled chlorocarboxymethylation/decarboxylation of the sulfobetaine-sulfinate formed in situ in two process steps, is illustrated by the following equations:

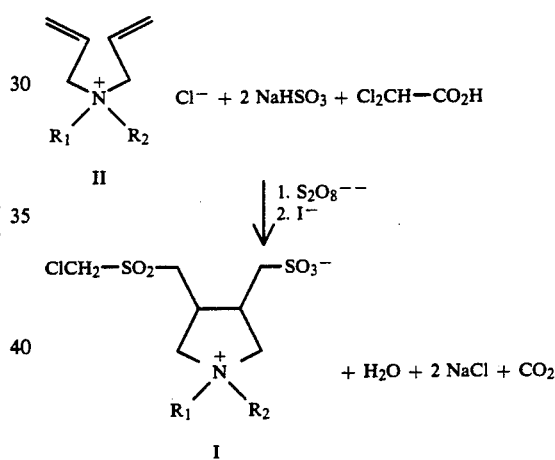

According to DD 225,128 A1, the sulfocyclosulfination of a diallylammonium salt proceeds with a maximum yield of sulfocyclosulfination product (sulfobetaine-sulfinate) only if pH conditions of around 2 are maintained. The adjustment to this pH is effected by addition of a mineral acid to the mixture of diallylammonium salt and hydrogen sulfite. Corresponding pH adjustments have hitherto not been carried out with dichloroacetic acid. It can therefore be regarded as a surprising finding that, for example, the addition of 1 mol of dichloroacetic acid to a mixture of 1 mol of diallylammonium salt and 2 mol of technical sodium hydrogen sulfite solution gives the optimum starting pH of around 2, i.e. conditions corresponding to the goal stated above. The order of combining the reactants is of no importance to the course of the reaction.

Depending on the quality of the sodium hydrogen sulfite solution used, slight pH fluctuations can occur. They can be corrected either by adding a small quantity of a mineral acid or by starting the reaction with a part quantity of the halogenocarboxylic acid and adding the remaining quantity of the halogenocarboxylic acid only during the reaction.

If, for example, tertiary diallylamines are used as the starting products of the reaction, these should preferably be dissolved in the dichloroacetic acid and, after addition of the hydrogen sulfite solution, the pH should be adjusted to the starting value with a mineral acid. Since, in the case of tertiary diallylamines and a starting pH of 2.5, the sulfocyclosulfination already proceeds to completion, less than the molar equivalent quantity of mineral acid is required for forming the diallylammonium salt.

The end products obtained in the overall reaction are then the metal sulfonates corresponding to formula I, depending on the metal hydrogen sulfite used. From the latter, the target product can then be liberated by addition of mineral acid.

For carrying out the first process step, 1 to 5 mol % of peroxodisulfate, relative to the diallylammonium salt employed, are added to the starting solution which has been prepared in this way and which should have a temperature of between 20° and 30° C., in order to initiate the sulfocyclosulfination reaction.

It has proved preferable here to add the peroxodisulfate in two portions, in order to achieve the most complete conversion possible, quantities of 2 times 2 mol %, relative to the diallylammonium salt employed, being fully sufficient in most cases.

Suitable peroxodisulfates are sodium, potassium or ammonium peroxodisulfate, which can be employed either as a solution or in powder form.

The initially pale yellow starting solution assumes a red to blood-red color after the addition of peroxodisulfate, but it considerably brightens shortly after passing through the temperature maximum.

To initiate the second process step, a catalytic quantity of a soluble iodide, for example sodium, potassium or ammonium iodide, is added to the reacting solution, and heating is continued with evaporative cooling until sulfinate is no longer detectable in the reacting solution by bromatometric titration of a sample.

When using a quantity of 14 to 20 mmol of sodium iodide, potassium iodide or ammonium iodide/mol of diallylammonium salt, complete conversions are achieved in the course of one to two hours. Whereas quantities of less than 14 mmol of the abovementioned iodides no longer display any catalytic action, quantities greater than 20 mmol further accelerate the reaction, but the crystalline target products later suffer a discoloration.

If, however, the alkylation of the sulfocyclosulfination product with dichloroacetic acid is carried out without added iodide, the desired reaction takes place in the initial phase. However, it slows down increasingly with progressing reaction time, so that complete conversion is not achievable even after long reaction times. However, precisely because the conversion remains incomplete, the target products can be separated from such complex mixtures, due to the polar character of the starting and end products, only with difficulty and incompletely or not at all.

A further surprising fact in this second process step is that the sulfocyclosulfination product of the diallylammonium salt can be chloromethylated at a low pH at the boil with decarboxylation, even though it is known [W. Jeblick and W. Bunge in "Ullmanns Encyklopädie der technischen Chemie (Ullmann's Encyclopedia of Industrial Chemistry)", volume 22 (1982), page 315] that under such conditions—low pH and high temperatures—sulfinic acids preferentially disproportionate to thiosulfonic S-esters and sulfonic acids.

For this reason, it was also regarded as necessary according to the state of the art to obtain chloromethyl sulfones by reacting the metal salts of sulfinic acids and dichloroacetates, evidently in order to preclude such disproportionation reactions.

A further advantage of the process according to the invention is that the reaction can be carried out in the acidic pH range with free dichloroacetic acid, the carbon dioxide resulting from the decarboxylation of the intermediate escaping in the gaseous form from the reaction mixture, whereas, according to the procedure of the state of the art, this remains as carbonate in the reaction product and would have to be additionally separated from the latter afterwards.

In a special embodiment of the process, it is possible also to carry out the second process step separately. For this purpose, for example, the pure sodium salts of previously isolated sulfobetaine-sulfinic acids can be directly reacted in the presence of iodide with the molar equivalent quantity of dichloroacetic acid. However, dichloroacetates can also be treated in an analogous manner with isolated sulfobetaine-sulfinic acids. In all cases, however, the reaction products thus obtained are identical to those which are obtained according to the two-stage synthesis process. This synthesis route has no process advantage in principle, since the starting sulfobetaine-sulfinates required for this purpose must first be prepared from the diallylammonium salts.

In summary, the advantage of the invention is a simple synthesis which makes the hitherto unknown chloromethylsulfonyl -sulfobetaines of the formula I directly accessible from diallylammonium salts without the isolation of intermediates. The starting materials used are intermediates which are available on an industrial scale and which can be caused to react in short reaction times by simple means.

The invention will be explained in more detail by the examples which follow.

EXAMPLES

Example 1

1,1-Dimethyl-3-chloromethylsulfonylmethyl-4-sulfomethyl-pyrrolidinium betaine ($R_1=R_2=CH_3$ in the general formula I)

a) 307.4 g (1 mol) of 52.6% aqueous dimethyldiallylammonium chloride solution, 129 g (1 mol) of dichloroacetic acid and 539 g (2.02 mol) of 39% technical sodium hydrogen sulfite solution are introduced into a 1.5 l sulfonation flask which is fitted with a stirrer, thermometer, reflux condenser and a heat source, and mixed with one another with stirring. This gives a solution, which is slightly turbid due to dichloroacetic acid which has remained partially undissolved, having a temperature of 21° C. and a starting pH of 1.7. To initiate the reaction, 4.56 g (2 mol %) of ammonium peroxodisulfate are then first added and 1.5 minutes later—the reaction solution has assumed a red color in the meantime and the reaction temperature has risen to 55° C.—a further 2 mol % of ammonium peroxodisulfate are added. The temperature maximum of 71° C. is already reached after one further minute. 2.55 g (17 mmol) of sodium iodide are added to the reaction solution and the latter is heated to the boil for 3 hours at 110° C. Already during the heating-up, the red reaction solution decolorizes, and it is pale yellow when the boiling point is reached. The reaction is quantitatively complete when the reaction intermediate, i.e. 1,1-dimethyl-3-sulfinatomethyl -4-sulfomethyl-pyrrolidinium betaine, is no longer detectable by bromoatometric titration of a sample of the reacting solution. The latter is allowed to cool and left to stand overnight for complete crystallization. For working-up, the crystal mass is filtered off sharply from the mother liquor with suction, the crystals are washed with a little water and twice with alcohol and, after drying in air, 200 g of a white, loose crystal powder are obtained, which can still be recrystallized from water for fine purification. Melting point: starting at 270° C. with decomposition. A further fraction of the target product can still be obtained by working up the mother liquor. $^{13}C$—NMR spectrum ($H_2O$/HCl; external standard tetramethylsilane=TMS; $\delta$=0.0 ppm):

The numerical data at the atom symbols correspond to the chemical shifts for the cis-configuration (3,4-positions) in ppm.

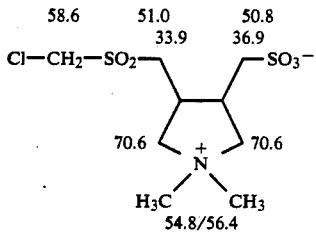

The N—CH$_3$ groups are not equivalent and, as in the case of the N—CH$_2$ groups, there is an additional signal splitting due to the $^{14}N$ quadrupole moment.

b) 307 g (1 mol) of 1,1-dimethyl-3-sulfinic acid methyl-4-sulfomethyl-pyrrolidinium betaine dihydrate (prepared from dimethyldiallylammonium chloride and sodium hydrogen sulfite; cf. DD 225,128 A1, Example 13), 121.2 g (1 mol) of 33% sodium hydroxide solution, 129 g (1 mol) of dichloroacetic acid, 3 g (20 mmol) of sodium iodide and 200 g of water are mixed with one another and heated to the boil for 3 hours. Crystals of the target product already precipitate after a short time from the colorless reaction solution. After cooling of the reaction solution, 302 g (94.5% yield) of chloromethylsulfonylsulfobetaine can be isolated.

The $^{13}C$—NMR spectrum of the product obtained is fully identical to that of the product prepared according to Example 1a.

EXAMPLE 2

3-Chloromethylsulfonylmethyl-4-sulfomethyl-pyrrolidinium betaine ($R_1=R_2=H$ in the general formula I)

The procedure followed is as in Example 1a, and a mixture at pH 2.3 of 19.4 g (0.2 mol) of diallylamine, 107.8 g (0.404 mol) of 39% technical sodium hydrogen sulfite solution and 25.8 g (0.2 mol) of dichloroacetic acid is reacted with two portions each of 0.92 g (2 mol %) of ammonium peroxodisulfate. The reaction temperature thus rises from 27° to 65° C. 0.45 g (3 mmol) of sodium iodide is added, and the reaction solution is heated to the boil for 3 hours and concentrated to a viscous, light-brown mass. After digesting with methanol and drying in air, 43 g of beige-colored crystals are obtained. Melting point starting at 200° C. with decomposition.

$^{13}C$—NMR spectrum (D$_2$O, external standard TMS=0.0 ppm)

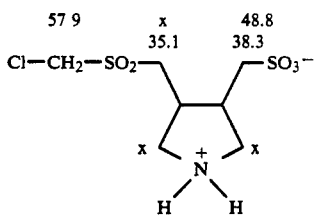

EXAMPLE 3

1-Dodecyl-3-chloromethylsulfonylmethyl-4-sulfomethylpyrrolidinium betaine ($R_1=H$; $R_2=C_{12}H_{25}$ in the general formula I)

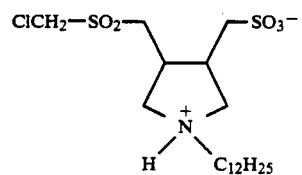

The procedure followed is as in Example 1a, and a mixture at pH 2.2 of 26.55 g (0.1 mol) of diallyldodecylamine, 12.9 g (0.1 mol) of dichloroacetic acid, 53.9 g (0.202 mol) of 39% technical sodium hydrogen sulfite solution and 3 g of 37% hydrochloric acid is reacted with two portions each of 0.46 g (2 mol %) of ammonium peroxodisulfate. The reaction temperature thus rises from 28° to 69° C.; the solution becomes viscous. After the addition of 0.3 g (2 mmol) of sodium iodide and heating at the boil for 3 hours, the initially lemon-yellow solution assumes a brownish color (release of iodine; the solution can be completely decolorized by adding a few drops of hydrogen sulfite solution) and is completely converted to a viscous, foaming solution of the target product.

We claim:

1. A 3-chloromethylsulfonylmethyl-4-sulfomethyl-pyrrolidinium betaine of the formula I

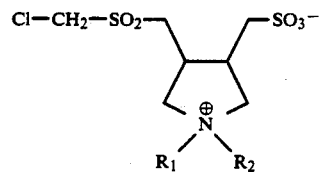

in which

R$_1$ and R$_2$ are hydrogen, a straight-chain or branched alkyl radical having 1 to 22 carbon atoms or a radical —CH$_2$CONH—alkyl.

2. A compound as claimed in claim 1, wherein R$_1$ and R$_2$ are —CH$_3$.

3. A compound as claimed in claim 1, wherein R$_1$ and R$_2$ are hydrogen.

4. A compound as claimed in claim 1, wherein R$_1$ is hydrogen and R$_2$ is C$_{12}$H$_{25}$.

5. A process for the preparation of a 3-chloro -methylsulfonylmethyl-4-sulfomethyl-pyrrolidinium betaine of the formula I as claimed in claim 1, which comprises reacting together in a solution a diallylammonium salt with a molar quantity of dichloroacetic acid and twice the molar quantity of a hydrogen sulfite in the presence of a catalytic quantity of a peroxodisulfate and heating in a second step, the reaction solution obtained, after the addition of a catalytic quantity of iodide, to the boil until the sulfinate content of the reacting solution has fallen to zero or the decarboxylation is complete.

6. The process as claimed in claim 5, wherein 1 to 5 mol % of peroxodisulfate, relative to the diallylammonium salt employed, are added as the catalyst in the first process step.

7. The process as claimed in claim 6, wherein the peroxodisulfate is added in two portions each of 2 mol %, relative to the diallylammonium salt employed.

8. The process as claimed in claim 5, wherein 14 to 20 mol of sodium iodide, potassium iodide or ammonium iodide/mol of diallylammonium salt are added as the catalyst in the second process step.

9. The process as claimed in claim 5, wherein the diallylammonium salt is a diallylammonium chloride of the formula II

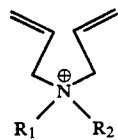

in which
  $R_1$ and $R_2$ are hydrogen, a straight-chain or branched alkyl radical having 1 to 22 carbon atoms or a radical —$CH_2$—CONH—alkyl.

10. The process as claimed in claim 5, wherein said hydrogen sulfite is sodium hydrogen sulfite.

11. The process as claimed in claim 5, wherein the peroxodisulfate is added in two portions each of 2 mol %, relative to the diallylammonium salt employed.

12. The process as claimed in claim 5, wherein said peroxodisulfate is sodium peroxodisulfate.

13. The process as claimed in claim 5, wherein said peroxodisulfate is potassium peroxodisulfate.

14. The process as claimed in claim 5, wherein said peroxodisulfate is ammonium peroxodisulfate.

* * * * *